United States Patent
Schoenmakers et al.

(10) Patent No.: US 11,401,559 B2
(45) Date of Patent: Aug. 2, 2022

(54) KIT AND METHOD FOR DETECTING BLADDER CANCER

(71) Applicant: LEICA BIOSYSTEMS NEWCASTLE LTD., Newcastle Upon Tyne (GB)

(72) Inventors: Saskia Schoenmakers, Newcastle Upon Tyne (GB); Harry Schrickx, Newcastle Upon Tyne (GB); Herman Volkers, Newcastle Upon Tyne (GB)

(73) Assignee: LEICA BIOSYSTEMS NEWCASTLE LTD, Newcastle Upon Tyne (GB)

( * ) Notice: Subject to any disclaimer, the term of this patent is extended or adjusted under 35 U.S.C. 154(b) by 160 days.

(21) Appl. No.: 16/533,015

(22) Filed: Aug. 6, 2019

(65) Prior Publication Data

US 2020/0102619 A1 Apr. 2, 2020

Related U.S. Application Data

(62) Division of application No. 15/118,266, filed as application No. PCT/IB2015/000919 on Feb. 11, 2015, now Pat. No. 10,370,720.

(60) Provisional application No. 61/939,137, filed on Feb. 12, 2014.

(51) Int. Cl.
*C12Q 1/68* (2018.01)
*C07H 21/04* (2006.01)
*C12Q 1/6886* (2018.01)
*C12Q 1/6841* (2018.01)

(52) U.S. Cl.
CPC .......... *C12Q 1/6886* (2013.01); *C12Q 1/68* (2013.01); *C12Q 1/6841* (2013.01); *C12Q 2600/118* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,174,681 B1 | 1/2001 | Halling et al. | |
| 6,280,929 B1 | 8/2001 | Gray et al. | |
| 6,376,188 B1 | 4/2002 | Halling et al. | |
| 6,573,042 B1* | 6/2003 | Wang | C12Q 1/6841 435/6.14 |
| 7,232,655 B2* | 6/2007 | Hailing | C12Q 1/6841 435/6.16 |
| 7,998,670 B2 | 8/2011 | Halling et al. | |
| 10,370,720 B2* | 8/2019 | Schoenmakers | C12Q 1/6886 |
| 2003/0087248 A1* | 5/2003 | Morrison | C12Q 1/6841 435/6.16 |
| 2009/0220955 A1 | 9/2009 | Verrant | |
| 2012/0141987 A1 | 6/2012 | Morrison | |

FOREIGN PATENT DOCUMENTS

| | | |
|---|---|---|
| EP | 1035215 | 9/2000 |
| WO | WO 02/066685 | 8/2002 |

OTHER PUBLICATIONS

D. Zheng et al. (Am. J. of Pathology, vol. 165, No. 1, pp. 63-69, Jul. 2004) (Year: 2004).*
Eguchi et al., "POS-02.12: Analysis of genome-wide copy number changes in bladder cancers using array-based comparative genomic hybridization", *Urology*, 70(Supplemental 3A): 236, 2007.
Hurst et al., "High-resolution analysis of genomic copy number alterations in bladder cancer by microarray-based comparative genomic hybridization", *Oncogene*, 23: 2250-2263, 2004.
International Search Report and Written Opinion issued in PCT/IB2015/000919, dated Sep. 28, 2015.
Klatte et al., "Absence of CD44 Expression is an Independent Predictor of Poor Outcome for Patients with Urothelial Bladder Cancer", *Journal of Urology*, 181(4): 309, 2009.
Van Rhijn et al., "Cytology and Urinary Markers for the Diagnosis of Bladder Cancer", *European Urology Supplements*, 8: 536-541, 2009.
Zheng et al., "TRIO Amplification and Abundant mRNA Expression is Associated with Invasive Tumor Growth and Rapid Tumor Cell Proliferation in Urinary Bladder Cancer", *American Journal of Pathology*, 165: 63-69, 2004.
Office Action issued in European Application No. 15731670.4, dated Dec. 12, 2017.

* cited by examiner

*Primary Examiner* — Jeanine A Goldberg
(74) *Attorney, Agent, or Firm* — Norton Rose Fulbright US LLP

(57) ABSTRACT

Methods and kits are provided for screening a patient for bladder cancer. Embodiments include those involving centromeric probes to chromosomes 3, 7, and 10 and a locus-specific probe to 5p15.

10 Claims, 1 Drawing Sheet

KIT AND METHOD FOR DETECTING BLADDER CANCER

CROSS-REFERENCE TO RELATED APPLICATIONS

This application is a divisional application of U.S. patent application Ser. No. 15/118,266, filed Aug. 11, 2006, which is a national phase application under 35 U.S.C. § 371 of International Application No. PCT/IB2015/000919 filed Feb. 11, 2015, which claims the benefit of priority to U.S. Provisional Patent Application No. 61/939,137, filed Feb. 12, 2014. The entire contents of each of the above-referenced disclosures are specifically incorporated herein by reference without disclaimer.

TECHNICAL FIELD

The present invention relates generally to a panel of labeled tumor markers and a method of using the same to diagnose bladder cancer.

BACKGROUND

Bladder carcinoma is the most common malignancy of the urinary tract. Approximately 380,000 new cases of bladder cancer (BC) occur around the world each year (Van Rhijn et al, Cytology and Urinary Markers for the Diagnosis of Bladder Cancer European Urology Supplements 8 (2009), 536-541), of which 70,000 are in the US. BC is the fourth most common cancer in men and eighth most common cancer in women. The worldwide age standardized incidence rate (ASR) is 10.1 per 100,000 for males and 2.5 per 100,000 for females.

Lifelong surveillance is required for bladder cancer patients who are initially diagnosed with noninvasive disease. In Europe, current patient monitoring protocols generally consist of regularly scheduled urethro-cystoscopy (UCS) as the gold standard and urine cytology as an adjunct. For the urological practice, in terms of cost reduction and convenience for patients, markers to detect recurrent disease would be particularly useful. Unfortunately, molecular urinary markers have not yet improved the combination of UCS and cytology with relation to detection of bladder tumors.

In the U.S., urine-based tests, particularly for low-grade lesions, have been developed for the detection and surveillance of urothelial carcinoma molecular markers on exfoliated cells in voided urine and are used in conjunction with urine cytology. The most prominent molecular markers include BTA Stat™ (Polymedco, Inc.), uCyt™/Immuno-Cyt™ (Scimedx Corp.), and NMP22™ (Alere). The UroVysion™ DNA-FISH test (Abbott Molecular, IL) is designed to detect aneuploidy for chromosomes 3, 7, 17, and loss of the 9p21 locus via fluorescence in situ hybridization (FISH) (see U.S. Pat. Nos. 6,174,681, 6,376,188, 7,232,655, and 7,998,670).

There remains a need for improved non-invasive bladder cancer tests.

SUMMARY OF THE INVENTION

It is an aspect of the invention to provide a method for screening for bladder cancer or precursor cells thereto in a subject. The method involves the use of in situ hybridization for detecting chromosomal abnormalities associated with bladder cancer. In this method, a set of labeled nucleic acid probes are hybridized to cells in a biological sample, preferably a urine sample or biopsy, to selectively detect a bladder cancer or precursor cells thereto in the sample. The hybridization pattern of the probes are then assessed and thereafter correlated with the presence or absence of an bladder cancer and/or precursor cells.

It is a further aspect of the present invention to provide a set of nucleic acid probes for use in the method of the present invention. The set of probes is characterized by the ability to selectively detect bladder cancer and/or precursor cells in the biological sample. The set comprises chromosomal probes complementary to target regions bearing chromosomal abnormalities associated with bladder cancer.

In a particular aspect of the present invention, the chromosomal probes comprise centromeric probes to chromosomes 3, 7, and 10 and a locus-specific probe to 5p15. In a preferred embodiment, the probes include satellite enumeration probes to chromosomes 3, 7, and 10 and a locus-specific probe to 5p15. In a more preferred embodiment, the probes include satellite enumeration probes to chromosomes 3, 7, and 10 and a probe specific for TERT (located at 5p15.3).

BRIEF DESCRIPTION OF THE DRAWINGS

This patent application file contains at least one drawing executed in color. Copies of this patent application with color drawing(s) will be provided by the Office upon request and payment of the necessary fee.

DETAILED DESCRIPTION

Figures 1A, 1B, 1C, 1D:
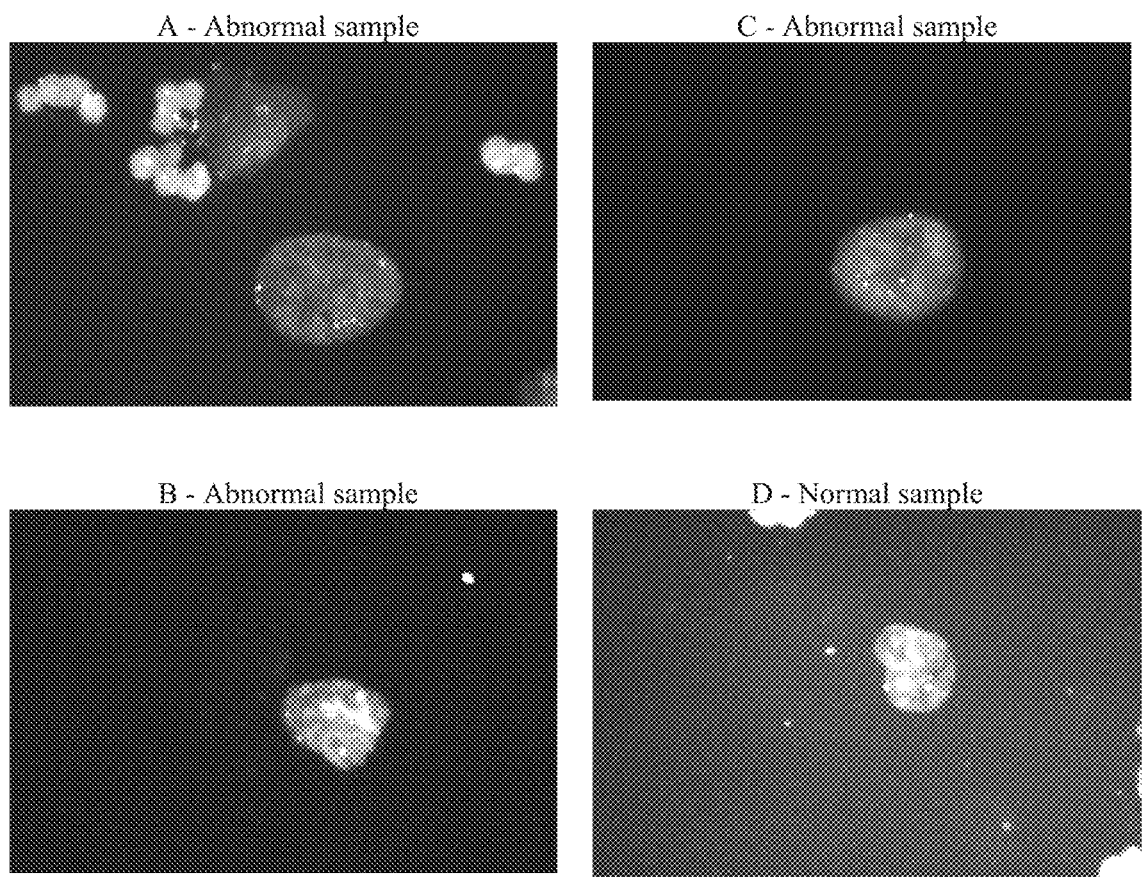
FIG. 1A-D show gray scale images of cells visualized with fluorescent probes according to the present invention.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The reference in this specification to any prior publication (or information derived from it) or to any matter which is known is not, and should not be taken as, an acknowledgment or admission or any form of suggestion that that prior publication (or information derived from it) or known matter forms part of the common general knowledge in the field of endeavor to which this specification relates.

It must be noted that, as used in the subject specification, the singular forms "a", "an" and "the" include plural aspects unless the context clearly dictates otherwise. Thus, for example, reference to "an agent" includes a single agent, as well as two or more agents; reference to "the composition" includes a single composition, as well as two or more compositions; and so forth.

A "probe" can be either a single nucleic acid or a collection of nucleic acid fragments (also a "probe set") whose hybridization to a probe target can be detected. The probe can be labeled as described below so that its binding to the target can be visualized. The probe is produced from some source of nucleic acid sequences, as for example, a collection of clones or a collection of polymerase chain reaction (PCR) products. The source nucleic acid may be processed in some way, as for example by removal of repetitive sequences (using procedures such as those described in U.S. 2009/0220955) or by blocking repetitive sequences with unlabeled nucleic acid having a complementary sequence, so that hybridization with the resulting probe produces staining of sufficient contrast on the target (such as described by Gray et al., U.S. Pat. No. 6,280,929).

A "probe target" is a nucleic acid sequence, typically in a sample being tested, to which the probe (or probe set) binds, preferably under high stringency conditions. [0013] As used herein, when two or more probes are mixed together, they produce a new probe which when hybridized to a target, produces a staining pattern that is a combination of the staining patterns individually produced by the component probes thereof. For example, if one probe of this invention produces a dot on chromosome 9, and another probe produces a band on chromosome 11, together the two probes form a probe which produces a dot/band staining pattern.

Probes that hybridize with centromeric DNA and locus-specific 5p15 DNA are available commercially, for example, from Leica Biosystems (Newcastle UK), Abbott Molecular (Des Plaines, Ill.), Molecular Probes, Inc. (Eugene, Oreg.), Cytocell (Oxfordshire, UK), etc. Alternatively, probes can be made non-commercially from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR).

Preferred centromeric probes for chromosomes 3, 7, and 10 include the Satellite Enumeration Probes available from Leica Biosystems. Other commercially available satellite enumeration (also known as Centromere Enumeration probes) can be used. [0016] Preferred locus-specific 5p15 probes include those directed to TERT, CTNND2, and CLPTM1L. The Poseidon™ Repeat Free™ TERT probe from Leica Biosystems is particularly preferred. The preferred target region for the locus-specific 5p15 probes is typically 150-250 kb, more preferably 190-210 kb.

It is of note that the various probes available from Leica Biosytems are smaller than their target regions because they have been processed using the Repeat Free™ process (which is generally described in U.S. 2009/022055). Generally, source DNA, which is a double-stranded DNA containing the target sequence, is selected. To obtain single-stranded DNA devoid of repetitive sequences, first an amplified whole-genome library is made from the source DNA according to standard procedures. The library obtained consists of randomly selected fragments ranging in size from approximately 200 to 500 base pairs. Each fragment consists of double-stranded DNA having PCR primer sequences at each end. Double-stranded DNA fragments are denatured by heating up to 95° C. or other means to obtain single-stranded DNA fragments. The resulting single-stranded DNA fragments contain repetitive sequences, unique sequences or a combination of unique and repetitive sequences. An excess of Cot DNA or other appropriate subtractor DNA that binds to repetitive sequences is added. Subsequent lowering of the temperature results in the formation of double-stranded DNA for only those fragments that contain repetitive sequences. Duplex Specific Nuclease (DSN) is added to allow digestion of double-stranded DNA. In one embodiment, the DSN enzyme is added for 2 hours at 65° C. The resulting composition contains mostly of (a) single-stranded DNA having only unique sequences and (b) digested DNA. The unique sequence, now single-stranded DNA with PCR primers at both ends, is used as a template to generate large amounts of the unique sequence for use in probe production. These repeat-depleted DNA sequences can be used as hybridization probes without the use of a blocking DNA.

In contrast, probes from other vendors such as Abbott Molecular and Agilent/Dako generally hybridize over a large area of the target region.

Fluorescent probes can be obtained from the above commercial probe vendors or can be made by labeling a commercial probe with a fluorescent tag. For example, FISH-Bright™ labeling kits (Leica Biosystems) can be used to directly label a probe with a Universal Linkage System (ULS™) which is a platinum compound linked to a fluorophore. Other conventional techniques such as nick translation, random priming, end labeling, etc. can also be used to insert a fluorescently labeled nucleotide into the probe.

The biological sample can be anything containing nucleus-bearing cells including but not limited to urine, blood, cerebrospinal fluid, pleural fluid, sputum, peritoneal fluid, bladder washings, oral washings, biopsy, tissue samples, touch preps, or fine-needle aspirates, and can be concentrated prior to use. Urine is a particularly useful biological sample. The cells can be selected by nuclear morphology including nucleus size and shape. Nuclear morphology can be assessed by DAPI, Hoechst or other suitable staining.

Cells can be harvested from the biological sample using standard techniques. For example, cells can be harvested by centrifuging the biological sample and resuspending the pelleted cells. The cells can then be fixed, as for example in acid alcohol solutions, acid acetone solutions, or aldehydes such as formaldehyde, paraformaldehyde, and glutaraldehyde.

Slides can be prepared by concentrating the fixed cell suspension and applying the concentrated suspension to slides such that the cells do not overlap. Cell density can be measured by a light or phase contrast microscope. For example, cells harvested from a 20 to 100 ml urine sample typically are resuspended in a final volume of about 100 to 200 μl of fixative.

Prior to in situ hybridization, chromosomal DNA contained within the cell is denatured. Denaturation typically is performed by incubating in the presence of high pH, heat (e.g., temperatures from about 70 to about 95° C.), organic solvents such as formamide and tetraalkylammonium halides, or combinations thereof. Denaturation conditions typically are established such that cell morphology is preserved.

After removal of denaturing chemicals or conditions, the centromeric and locus-specific probes are annealed to the chromosomal DNA under hybridizing conditions (conditions that facilitate annealing between a probe and target chromosomal DNA). Hybridization conditions vary, depending on the concentrations, base compositions, complexities, and lengths of the probes, as well as salt concentrations, temperatures, and length of incubation. The higher the concentration of probe, the higher the probability of forming a hybrid.

Non-specific binding of chromosomal probes to DNA outside of the target region can be removed by a series of washes. Temperature and concentration of salt in each wash depend on the desired stringency. The method of the present invention is preferably performed under high stringency conditions (i.e., washes are carried out at about 65 to about 80° C., using 0.2 to about 2×SSC, and about 0.1% to about 1% of a non-ionic detergent such as Nonidet P-40 (NP40).

Bladder cancer is screened for in a biological sample by determining the presence or absence of aneusomy (i.e., of a non-disomic number of one or more target sequences).

According to one embodiment of the present invention, when (i) more than two copies of the 5p15 region or (ii) more than two copies of at least two of the centromeric regions of chromosomes 3, 7, and 10 are present in the sample, then the patient likely has bladder cancer. In another embodiment, when (i) more than two copies of the 5p15 region and (ii) more than two copies of at least two of the centromeric regions of chromosomes 3, 7, and 10 are present in the sample, then the patient likely has bladder cancer. After a cell is selected based on one or more of the stated criteria, the presence or absence of aneusomy is assessed by examining the hybridization pattern of the chromosomal probes (i.e. the number of signals for each probe) in each selected cell, and recording the number of chromosome signals. This step is repeated until the hybridization pattern has been assessed in at least 4 cells, if all 4 cells are aneusomic. In a typical assay, the hybridization pattern is assessed in about 20 to about 25 selected cells.

Cells with more than two copies of two or more portions of chromosomes 3, 7 and 10 (i.e., gains of copy number of target sequences on multiple chromosomes) are considered cancer-positive. Samples containing about 20 selected cells and at least about 4 test positive cells typically are considered cancer-positive. If less than about 4 test-positive cells are found, the number of copies of the chromosome region 5p15 is determined. A cancer-positive result also is indicated if more than 15% and preferably 25% of the cells demonstrate gain or amplification of the specific chromosome region 5p15.

The methods described herein can be used to screen patients for cancer, or can be used to monitor patients diagnosed with cancer. The methods described herein can be used alone or in conjunction with other tests, such as the hemoglobin dipstick test. For example, a patient having an increased risk of bladder cancer can be screened for bladder cancer by testing for hemoglobin in the urine, i.e., hematuria. During such a screening process, patients without hematuria do not need further analysis and instead are re-examined for hematuria in an appropriate amount of time, e.g., at their annual check-up. Samples from patients with hematuria are further analyzed using the methods described herein. In general, a set of chromosomal probes is hybridized with the biological sample, a subset of cells is selected, and the presence of aneusomic cells is determined in the selected cells. Patients that have aneusomic cells are further examined, for example by cystoscopy, and can receive appropriate treatment if necessary. After treatment, patients are monitored for cancer recurrence using the methods described herein.

The superior specificity of the methods described herein indicate that this technique could replace cytology for the detection and monitoring of cancers such as bladder cancer. The majority of patients with bladder cancer will have detectable aneusomic cells and can be monitored for treatment efficacy, and tumor recurrence/progression with the methods described herein. A small proportion of patients with cystoscopic or biopsy evidence of bladder cancer (primarily those with low grade, non-invasive tumors) may not have detectable aneusomic cells in their urine. These patients (i.e. those with low-grade papillary tumors) are at very low rate of tumor progression and may be conveniently monitored by a combination of the methods described herein and cystoscopy. The appearance of aneusomic cells in the urine of these patients may herald the development of a more aggressive tumor in this subset of patients. The high sensitivity and specificity of the FISH test described herein for aggressive bladder cancers may help reduce the frequency of cystoscopy.

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features. [0031] Certain embodiments of the invention will now be described with reference to the following examples which are intended for the purpose of illustration only and are not intended to limit the scope of the general invention hereinbefore described.

EXAMPLES

Materials and Methods

Preparation of samples for testing: Urine samples were obtained from patients and centrifuged in 50 ml tubes for 10 min at 600 g. The supernatant was removed, the remaining pellet was dissolved in 10 ml 1×PBS, and the resulting suspension was transferred to a 15 ml tube. Following centrifugation for 10 min at 600 g, the supernatant was again removed and 10 mL of ThinPrep™ CytoLyt™ Solution ("CytoLyt", a methanol-based, buffered preservative solution available from Hologic, Inc., MA) was added. The suspension was then preserved at −20° C.

Prior to testing, the samples in CytoLyt were warmed to room temperature. Sediments were transferred to a 15 ml tube and centrifuge for 5 min at 1200 rpm using a swing-out rotor. After the supernatant was removed, the remaining pellet was suspended twice with 5 ml of fixative (3× methanol: 1× acetic acid) and centrifuged for 5 min at 1200 rpm using a swing-out rotor. Thereafter, the pellet was resuspended in 50-500 μl (depends on pellet size) of fixative (3× methanol: 1× acetic acid) and stored at −20° C.

Slides were prepared by dropping x μl of fixed sample on a slide according to the following table:

| Humidity % | μl |
| --- | --- |
| 40-50 | 10 |
| 50-60 | 7 |
| 60-80 | 5 |

Thereafter, the slides were air dried at room temperature and subsequently dried on a Thermobrite™ slide processor (Leica Biosytems, Richmond Ill.) for 10 min at 80° C. followed by a cool down to 30° C. 0.125% Pepsin in 0.01 N HCl was added for 10 min at 37° C., followed by 1% Formaldehyde in 1×PBS for 10 min at room temperature, followed by 1×PBS for 2 min at room temperature. The slides were then dehydrated using 70/85/100% Ethanol and allowed to air dry.

FISH assay: The following Poseidon™ Repeat Free™ FISH probes were obtained from Leica Biosystems:

| Target region: | | Size* (bp) | Label | Color |
| --- | --- | --- | --- | --- |
| TERT | chr5: 1.318.107-1,509,826 | 191.720 | Platinum Bright™ 495 | Green |

| Target region: | Size* (bp) | Label | Color |
|---|---|---|---|
| TERT chr5: 1.116.186-1,318,084 | 201.899 | Platinum Bright ™ 495 | Green |
| SE3 | | Platinum Bright ™ 415 | Blue |
| SE7 | | Platinum Bright ™ 530 | Gold |
| SE10 | | Platinum Bright ™ 590 | Dark Red |

*This is the size of the target region before the Repeat Free process ™ is used to generate the probe set that this then labelled.

All probes were applied to the slides, covered with a cover slip and sealed with rubber cement (fixogum). The slides were then incubated at 75° C. for 5 min and overnight at 37° C. in a Thermobrite™ (Leica, Richmond Ill.). The fixogum and coverslip were gently removed and the slides were incubated at 72° C. for 2 min in 0.4×SSC/0.3% NP-40 then at room temperature for 2 min in 2×SSC/0.1% NP-40. Anti-fade/DAPI was added. The slides were coverslipped with a coverslip (24 mm×50 mm) and analysed.

Thirty-two (32) urine sediments (samples) were received from a clinical laboratory. The samples had been collected, pelleted, dissolved in PreservCyt™ (a methanol based, buffered preservative solution available from Hologic, Inc., MA) and stored at −20° C. according to the routine protocol described above. During prior routine clinical testing using Abbott Molecular's Urovysion™ kit, 20 samples were reported as "abnormal" and 12 as "normal."

All samples were reevaluated using the probe described above. Eight of the "abnormal" samples were also reevaluated using the Urovysion™ kit. The probe of the present invention provided the same results as the Urovysion™ kit.

Two samples previously identified as "abnormal" retested negative with both the probe of the present invention and the Urovysion™ kit. It is believed that the very low number of epithelia cells in these samples led to the negative result in retesting.

One sample previously identified as "abnormal" showed amplification with the probe of the present invention, but no amplification when retested with Urovysion™. Again, it is believed that the very low number of epithelia cells in these samples resulted in the inconsistent readings.

Eighteen of the twenty "abnormal" samples showed aneusomy (i.e., non-disomic copy numbers of target sequences) in a small number of nuclei. Exemplary results are shown in FIG. 1 A-D. That is, eighteen of the "abnormal" samples had results indicative of bladder cancer using both the probe of the present invention as well as the Urovysion™ kit. All eighteen aneusomy samples show copy-number gains of all four markers. Stand-alone amplification (i.e., increased copy number) of the 5p15 region was not observed in the test set.

Three of the 12 samples identified as "normal" in routine diagnostics could not be evaluated, due to the absence of cells after reprocessing. Nine samples showed a normal pattern.

The invention claimed is:

1. A kit comprising a set of probes consisting of fluorescently labeled centromeric probes to chromosomes 3, 7, and 10 and a fluorescently labeled locus-specific probe to 5p15 that specifically binds TERT or CLPTM1L.

2. The kit of claim 1, wherein the locus-specific probe to 5p15 binds to TERT.

3. The kit of claim 1, wherein the locus-specific probe to 5p15 binds to CLPTM1L.

4. The kit of claim 1, wherein the locus-specific probe to 5p15 targets a genomic region that is about 150-250 kb.

5. The kit of claim 1, wherein the locus-specific probe to 5p15 targets a genomic region that is about 190-210 kb.

6. The kit of claim 1, wherein the locus-specific probe to 5p15 is depleted of repetitive sequences.

7. The kit of claim 1, wherein the locus-specific probe to 5p15 contains repetitive sequences.

8. The kit of claim 1, wherein the centromeric probes are satellite enumeration probes.

9. The kit of claim 1, wherein the centromeric probes and locus-specific probe are suspended in hybridization buffer.

10. A kit comprising a set of probes consisting of fluorescently labeled centromeric probes to chromosomes 3, 7, and 10 and a fluorescently labeled locus-specific probe to 5p15 that specifically binds TERT, wherein the centromeric probes and locus-specific probe are suspended in hybridization buffer.

* * * * *